United States Patent
Kapre et al.

(10) Patent No.: US 12,239,697 B2
(45) Date of Patent: *Mar. 4, 2025

(54) VIRUS-LIKE PARTICLE CONJUGATES

(71) Applicant: Inventprise, LLC, Redmond, WA (US)

(72) Inventors: Subhash V. Kapre, Redmond, WA (US); Anup K. Datta, Renton, WA (US)

(73) Assignee: Inventprise, Inc., Redmond, WA (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/857,303

(22) Filed: Jul. 5, 2022

(65) Prior Publication Data

US 2023/0093700 A1    Mar. 23, 2023

Related U.S. Application Data

(63) Continuation of application No. 16/435,502, filed on Jun. 9, 2019, now Pat. No. 11,389,519.

(60) Provisional application No. 62/683,787, filed on Jun. 12, 2018, provisional application No. 62/683,543, filed on Jun. 11, 2018.

(51) Int. Cl.
| | |
|---|---|
| *A61K 39/12* | (2006.01) |
| *A61K 39/108* | (2006.01) |
| *A61K 39/39* | (2006.01) |
| *A61K 47/65* | (2017.01) |
| *C07K 14/025* | (2006.01) |
| *C12N 7/00* | (2006.01) |

(52) U.S. Cl.
CPC .......... *A61K 39/0258* (2013.01); *A61K 39/12* (2013.01); *A61K 39/39* (2013.01); *A61K 47/65* (2017.08); *C07K 14/025* (2013.01); *C12N 7/00* (2013.01); *C12N 2710/20023* (2013.01)

(58) Field of Classification Search
None
See application file for complete search history.

(56) References Cited

U.S. PATENT DOCUMENTS

| | | |
|---|---|---|
| 6,290,967 B1 | 9/2001 | Volkin et al. |
| 6,922,172 B2 | 7/2005 | Oshiyama et al. |
| 7,374,766 B1 | 5/2008 | Aguilar Rubido |
| 7,709,010 B2 | 5/2010 | Bryan et al. |
| 8,192,746 B2 | 6/2012 | Caufield et al. |
| 8,784,826 B2 | 7/2014 | Borkowski et al. |
| 9,109,007 B2 | 8/2015 | Kyle et al. |
| 9,439,958 B2 | 9/2016 | Arntzen et al. |
| 10,159,728 B2 | 12/2018 | Kapre |
| 10,688,720 B2 | 6/2020 | Kapre |
| 10,729,763 B2 | 8/2020 | Kapre |
| 10,758,606 B2 | 9/2020 | Kapre |
| 11,389,519 B2 * | 7/2022 | Kapre ............... C12N 7/00 |
| 2004/0228879 A1 | 11/2004 | Deschamps |
| 2007/0083024 A1 | 4/2007 | Ebara |
| 2008/0279926 A1 * | 11/2008 | Vandepapeliere ..... A61K 39/00 424/209.1 |
| 2009/0081202 A1 | 3/2009 | Fischer et al. |
| 2009/0181044 A1 | 7/2009 | Apt et al. |
| 2009/0279926 A1 | 11/2009 | Yahagi |
| 2010/0093855 A1 | 4/2010 | Luskey et al. |
| 2010/0260792 A1 * | 10/2010 | Murata ............... A61P 11/00 435/243 |
| 2012/0308592 A1 | 12/2012 | Chackerian et al. |
| 2013/0095134 A1 | 4/2013 | Arntzen et al. |
| 2013/0331548 A1 | 12/2013 | Nakaar et al. |
| 2014/0056933 A1 | 2/2014 | Renner et al. |
| 2016/0228532 A1 | 8/2016 | Bhambhani |
| 2017/0065704 A1 | 3/2017 | Kapre |
| 2017/0095577 A1 | 4/2017 | Woodard |
| 2017/0274063 A1 | 9/2017 | Carra et al. |
| 2018/0169262 A1 | 6/2018 | Lu |

FOREIGN PATENT DOCUMENTS

| | | |
|---|---|---|
| CA | 2352777 | 9/2009 |
| CN | 1332749 | 1/2002 |
| CN | 102747047 | 10/2012 |
| WO | WO2000/32229 | 6/2000 |
| WO | WO2006/082530 | 8/2006 |
| WO | WO2007/116028 | 10/2007 |
| WO | WO2008/094200 | 8/2008 |
| WO | WO2010001409 | 1/2010 |
| WO | WO2012/177970 | 12/2012 |
| WO | WO2014/092378 | 6/2014 |
| WO | WO2016/022916 | 2/2016 |

OTHER PUBLICATIONS

Office action for KR Application No. 10-2020-7037878 dated Nov. 21, 2023.
Office action for KR Application No. 10-2020-7037878 dated Nov. 21, 2023 (translated).
Office action for JP Application No. 2020-568688 dated Feb. 21, 2023.
Office action for JP Application No. 2020-568688 dated Feb. 21, 2023 (translated).
International Search Report and Opinion for PCT/US2019/36243 dated Aug. 28, 2019.
Schellenbacher et al., Chimeric L1-L2 Virus-Like Particles as Potential Broad-Spectrum Human Papillomavirus Vaccines, Journal of Virology 83(19):10085-10095 (Sep. 8, 2009).
Roberts MJ, Bentley MD, Harris JM. Chemistry for peptide and protein PEGylation. Adv Drug Deliv Rev. Jun. 17, 2002:54(4):459-76. doi: 10.1016/s0169-409x(02)00022-4. PMID: 12052709. (Year: 2002).
Examination Report for JP Application No. 2020-568688 dated Mar. 1, 2022.
Examination Report for JP Application No. 2020-568688 dated Mar. 1, 2022 (translated).

(Continued)

*Primary Examiner* — Stacy B Chen
(74) *Attorney, Agent, or Firm* — Remenick PLLC

(57) ABSTRACT

This invention is directed to immunogenic composition, conjugates, virus-like particles (VLP) compositions, vaccines and methods directed to the treatment and/or prevent of infection by Human Papillomavirus.

30 Claims, 4 Drawing Sheets

(56) References Cited

OTHER PUBLICATIONS

Examination report for AU Application No. 2019/287443 dated Apr. 4, 2022.
Examination report for ID Application No. P00202009616 dated May 23, 2022.
Examination report for ID Application No. P00202009616 dated May 23, 2022 (translated).
Garry L. Morefield, A Rational Systemic Approach for the Development of Vaccine Formulations, The AAPS Journal, 13(2):191-200, Feb. 23, 2011.
Lihua Shen, Efficient Encapsulation of Fe3O4 Nanoparticles into Genetically Engineered Hepatitis B Core Virus-Like Particles through a Specific Interaction for Potential Bioamplifications, Small vol. 11(9-10):1190-1196, Mar. 1, 2015.
Subrat Kumar Panda, Recombinant Hepatitis E Virus Like Particles can Function as RNA Nanocarriers, Journal of Nanobiotechnology 13(1):44, Jun. 24, 2015.
Schwardz et al. Development of virus-like particles for diagnostic and prophylactic biomedical applicationsWiley Interdiscip Rev Nanomed Nanoblotechnol. Sep. 2015 ; 7(5): 722-785.
Beterams et al. Packaging of up to 240 subunits of a 17 κDa nuclease into the recombinant hepatitis B virus capsids FEBS Letters 481 (2000) 169-176.
Tumban et al. A Pan-HPV Vaccine Based on Bacteriophage PP7 VLPs Displaying Broadly Cross-Neutralizing Epitopes from the HPV Minor Capsid Protein, L2. PLoS One, 2011, 6(8): e23310.
Tindle et al. Chimeric hepatitis B core antigen particles containing B- and Th-epitopes of human papillomavirus type 16 E7 protein induce specific antibody and T-helper responses in immunized mice. Virology 1994;200:547-557.
Kumru et al. Vaccine instability in the cold chain: Mechanisms, analysis and formulation strategies. Biologicals 42 (2014) 237-259.
Zhu et al. Hepatitis B virus surface antigen as delivery vector can enhance Chlamydia trachomatis MOMP multi-epitope immune response in mice. Appl Microbiol Biotechnol (2014) 98:4107-4117.
K. Roose et al. "Hepatitis B core-based virus-like particles to present heterologous epitopes" *Expert Rev. Vaccines* 12(2), 183-198 (2013).
N.V. Ravin et al., "Development of a candidate influenza vaccine based on virus-likeparticles displaying influenza M2e peptide into the immunodominantloop region of hepatitis B core antigen: Insertion of multiple copies ofM2e increases immunogenicity and protective efficiency" Vaccine 33 (2015) 3392-3397.
Liska et al. Evaluation of a recombinant human gelatin as a substitute for a hydrolyzed porcine gelatin in a refrigerator-stable Oka/Merck live varicella vaccine. Journal of Immune Based Therapies and Vaccines 2007, 5:4.

Jason D. Fiedler et al., "Engineered Mutations Change the Structure and Stability of a Virus-Like Particle" *Biomacromolecules*, 13 (8), pp. 2339-2348 (2012).
Schwarz et al., Development of virus like particles for diagnostic and prophylactic biomedical applications, Wiley Interdisciplin Rev. Nanomed Nanobiotechnol. Sep. 2015 7(5):722-735.
Beterams et al., Packaging of up to 240 subunits of a 17 kDa nuclease into the interior of recombinant hepatitis B virus capsids FEBS Letters 481 (2000) 169-176.
A.C. Tissot et al., Versatile Virus Like Particle Carrier for Epitope Based Vaccines, PlusOne 5(3):e9809 (Mar. 2010).
"Virus Like Particles: The Next Step in Gene Therapy" European Commission Report CPCH18603459, Aug. 14, 2013.
Qiudong Su et al., "Immune Responses to HBsAg Conjugated to Protein D of Non-Typeable Haemophilus influenzae in Mice" Plos One DOI: 10.1371/journal.pone.0117736 Feb. 17, 2015.
J.T. Bryan, "Developing an HPV vaccine to prevent cervical cancer and genital warts" Vaccine (2007), doi:10.1016/j.vaccine.2007.01.013.
G.T. Jennings et al., "The coming of age of virus-like particle vaccines" Biological Chemistry vol. 389, No. 5, Jan. 1, 2008.
A. Naskalska "Virus Like Particles as Immunogens and Universal Nanocarriers" Polish Journal of Microbiology vol. 64, No. 1, pp. 3-13, 2015.
Office action for KR Application No. 10-2020-7037878 dated May 9, 2023.
Office action for KR Application No. 10-2020-7037878 dated May 9, 2023 (translated).
Lyn H. Jones, "Recent Advances in the Molecular Design of Synthetic Vaccines" Nature Chemistry vol. 7, Nov. 20, 2015.
Office action for KR Application No. 10-2020-7037878 dated Apr. 24, 2024.
Office action for KR Application No. 10-2020-7037878 dated Apr. 24, 2024 (translated).
Office action for JP Application No. 2020-568688 dated Sep. 20, 2022.
Office action for JP Application No. 2020-568688 dated Sep. 20, 2022 (translated).
Office action for ID Application No. P00202009616 dated Oct. 21, 2022.
Office action for ID Application No. P00202009616 dated Oct. 21, 2022 (translated).
Wang JW, Roden RB. Virus-like particles for the prevention of human papillomavirus-associated malignancies. Expert Rev Vaccines. Feb. 2013;12(2):129-41. doi: 10.1586/erv.12.151. PMID: 23414405; PMCID: PMC3835148.
Office action for CN Application No. 201980039227.8 dated Sep. 23, 2024.
Office action for CN Application No. 201980039227.8 dated Sep. 23, 2024 (translated).

\* cited by examiner

| LINKER STRUCTURE | CHEMICAL STRUCTURES/KD OR Å USED |
|---|---|
| 1. NH2-PEG-NH2/NHS | $H_2N-(CH_2CH_2O)_n-CH_2CH_2-NH_2$<br>1K and 3.5K |
| 2. NHS/NH2-PEG-COOH | $H_2N-CH_2CH_2-PEG-C(=O)-OH$<br>1K AND 3.5K |
| 3. Mal-PEG-NH2 | Maleimide$-CH_2CH_2-C(=O)-NH-[CH_2CH_2O]_n-CH_2-NH_2$<br>1K AND 3.5K |
| 4. Mal-PEG-NHS | Maleimide$-CH_2CH_2-PEG-C(=O)-O-$NHS<br>1K AND 3.5K |
| 5. SH-PEG-NH2 | $HS-(CH_2CH_2O)_n-CH_2CH_2-NH_2$<br>1K AND 3.5K |
| 6. ADH | $H_2N-NH-C(=O)-(CH_2)_4-C(=O)-NH-NH_2$ |
| 7. HZ-PEG-HZ | $NH_2NHC(=O)CH_2O(CH_2CH_2O)_nCH_2C(=O)NHNH_2$<br>HYDRAZIDE-PEG-HYDRAZIDE<br>1K AND 3K |
| 8. 2-IMINO-THILANE | 2-iminothiolane •HCl |
| 9. SMPH | SMPH structure<br>SMPH<br>SUCCINIMIDYL 6-[(β-MALEIMIDOPROPIONAMIDO)HEXANOATE]<br>MW 379.36 SPACER ARM 14.2 Å |
| 10. SH-PEG-COOH | $HS-CH_2CH_2-O-[CH_2CH_2O]_n-CH_2-C(=O)-OH$<br>1K AND 3K |

FIG. 1

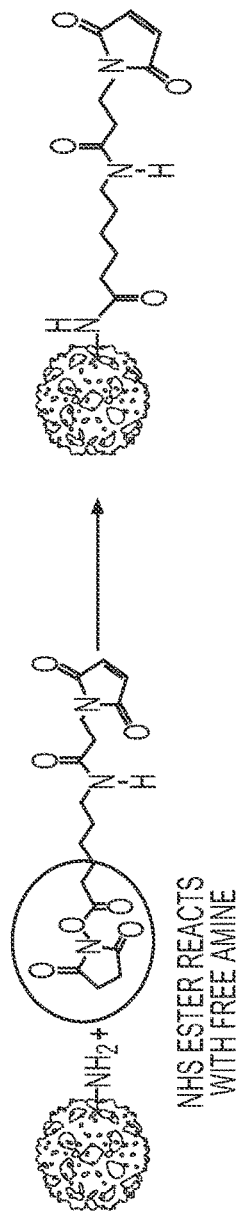
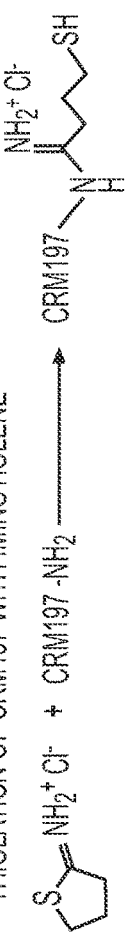
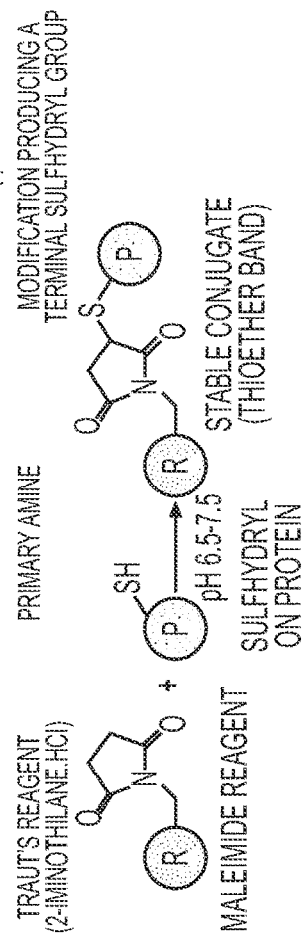
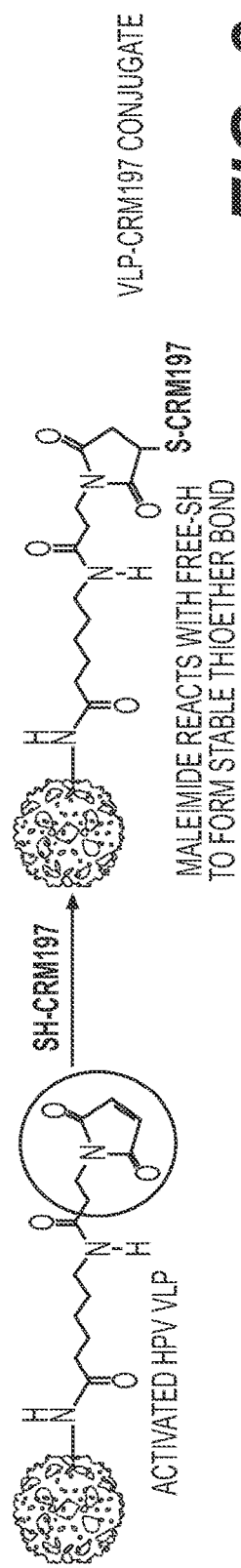
FIG. 3

VIRUS-LIKE PARTICLE CONJUGATES

REFERENCE TO RELATED APPLICATIONS

This application is a continuation of U.S. application Ser. No. 16/435,502 filed Jun. 9, 2019, which issued as U.S. Pat. No. 11,389,510 on Jul. 19, 2022, and claims priority to U.S. Provisional Application No. 62/683,787 filed Jun. 12, 2018, and U.S. Provisional Application No. 62/683,543 filed Jun. 11, 2018, the entirety of each of which is incorporated by reference.

BACKGROUND OF THE INVENTION

1. Field of the Invention

This invention is directed to immunogenic composition, conjugates, virus-like particles (VLP) compositions, vaccines and methods directed to the treatment and/or prevent of infection by Human Papillomavirus.

2. Description of the Background

Human Papillomavirus (HPV) is a double stranded DNA virus, which targets the basal cells of squamous epithelia for infection. HPV's circular DNA genome is composed of two major oncogenes, E6 and E7, and two major structural protein genes, L1 and L2. Most conventional vaccines are developed based on these components. The L1 protein of HPV expressed recombinantly in vitro self-assembles into virus-like particles (VLPs). VLPs have HPV type-specific conformational neutralizing epitopes and are used for the development of VLP-based vaccine products. Typically, VLPs are recombinantly expressed in yeast, bacterial, or insect cell expression systems.

Two HPV vaccines are currently on the market, GARDASIL (Merck and Co. Inc.) and Cervarix (GSK). The composition and dose of the GARDASIL vaccine comprises HPV VLP L1 protein containing 6,11,16,18,1, 33, 45, 52,58, a total of 9-serotypes and an aluminum adjuvant. The VLPs are present in an amount of 20-40 µg each per dose. The vaccine is administered as a 3-dose regimen according to a 0, 2, and 6-month schedule. The Cervarix vaccine comprises HPV VLPs 16 and 18 L1 proteins, and an adjuvant containing aluminum hydroxide and MPLA (3D-MPL). The VLPs are present at 20 µg each per dose. This vaccine is also administered as a 3-dose regimen according to a 0, 2, and 6-month schedule.

The cost of vaccine and the number of doses remain a main block in immunizing the population in developing world. Thus, a lower cost and lower dose vaccine is in great need throughout the world.

SUMMARY OF THE INVENTION

The present invention overcomes the problems and disadvantages associated with current strategies and designs and provides new immunogenic compositions, method of manufacturing immunogenic compositions, and methods of treated and preventing infections with the immunogenic compositions.

One embodiment of the invention is directed to immunogenic compositions such as a vaccine comprising virus-like particles (VLPs) obtained or derived from L1 and/or L2 proteins of Human papilloma virus (HPV), conjugated with a spacer arm and a carrier protein. Preferably the HPV comprises serotype 6, 11, 16, 18, 31, 33, 45, 52, and/or 58. Preferably the spacer arm comprises a hetero- or homo-bifunctional or multifunctional spacer arm, or in particular, comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$. Preferably the carrier protein comprises tetanus toxoid, diphtheria toxoid, CRM197, tetanus toxoid fragments (TTHc), *N. meningitidis* protein PorB, RSV virus proteins, *B. pertussis* proteins, *pertussis* toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof. Preferably the immunogenic composition comprises an adjuvant, and preferably the adjuvant comprises aluminum salt, calcium phosphate, a liposome of monophosphoryl lipid A (MPLA), saponin QS-21, TLR ligands, and/or a potent TLR4/7/8/9 agonists. Preferred aluminum salts include one or more of aluminum phosphate, aluminum sulfate and/or aluminum hydroxide. Preferably the immunogenic composition, when administered to a patient, boosts the efficacy of a conventional vaccine.

Another and related embodiment of the invention comprises an immunogenic composition as described herein wherein the VLP is obtained or derived from HPV L1 protein or HPV L2 protein and the carrier protein is CRM197.

Another and related embodiment of the invention comprises an immunogenic composition as described herein wherein the VLPs are bi-valent L1 VLP conjugates, the HPV is serotype 16 and/or 18, and the carrier protein is CRM197.

Another and related embodiment of the invention comprises an immunogenic composition as described herein wherein the VLPs are bi-valent L1 VLP conjugates, the HPV is serotype 6 and/or 11, and the carrier protein is CRM197.

Another and related embodiment of the invention comprises an immunogenic composition as described herein wherein the VLPs are bi-valent L1 VLP conjugates, the HPV is serotype 31 and/or 33, and the carrier protein is CRM197.

Another and related embodiment of the invention comprises an immunogenic composition as described herein wherein the VLPs are bi-valent L1 VLP conjugates, the HPV is serotype 45 and/or 52, and the carrier protein is CRM197.

Another and related embodiment of the invention comprises an immunogenic composition as described herein wherein the VLPs are bi-valent L1 VLP conjugates, the HPV is serotype 58, and the carrier protein is CRM197.

Another and related embodiment of the invention comprises an immunogenic composition as described herein wherein the VLPs comprise L1 protein conjugated to L2 protein, and the carrier protein is CRM197.

Another and related embodiment of the invention comprises the process of manufacturing and using the immunogenic compositions of the disclosure. Preferably the immunogenic compositions and stable and provide protection against infections at lower doses or less frequently than are available using conventional immunogenic compositions.

Other embodiments and advantages of the invention are set forth in part in the description, which follows, and in part, may be obvious from this description, or may be learned from the practice of the invention.

DESCRIPTION OF THE FIGURES

FIG. 1 Bi-functional spacer arm for activation of CRM197; Mal-Maleimide, NHS-Succinimide, PEG-Polyethylene glycol derivatives, ADH-Adipic acid di-hydrazide, HZ-hydrazide, 1k and 3K-Mn 1000 and 3500, FIG. 2 Schematic of the mechanism of action of VLP.

FIG. 3 Schematic of conjugation of VLP with carrier protein CRM197 with a spacer arm.

DESCRIPTION OF THE INVENTION

Figure 2:
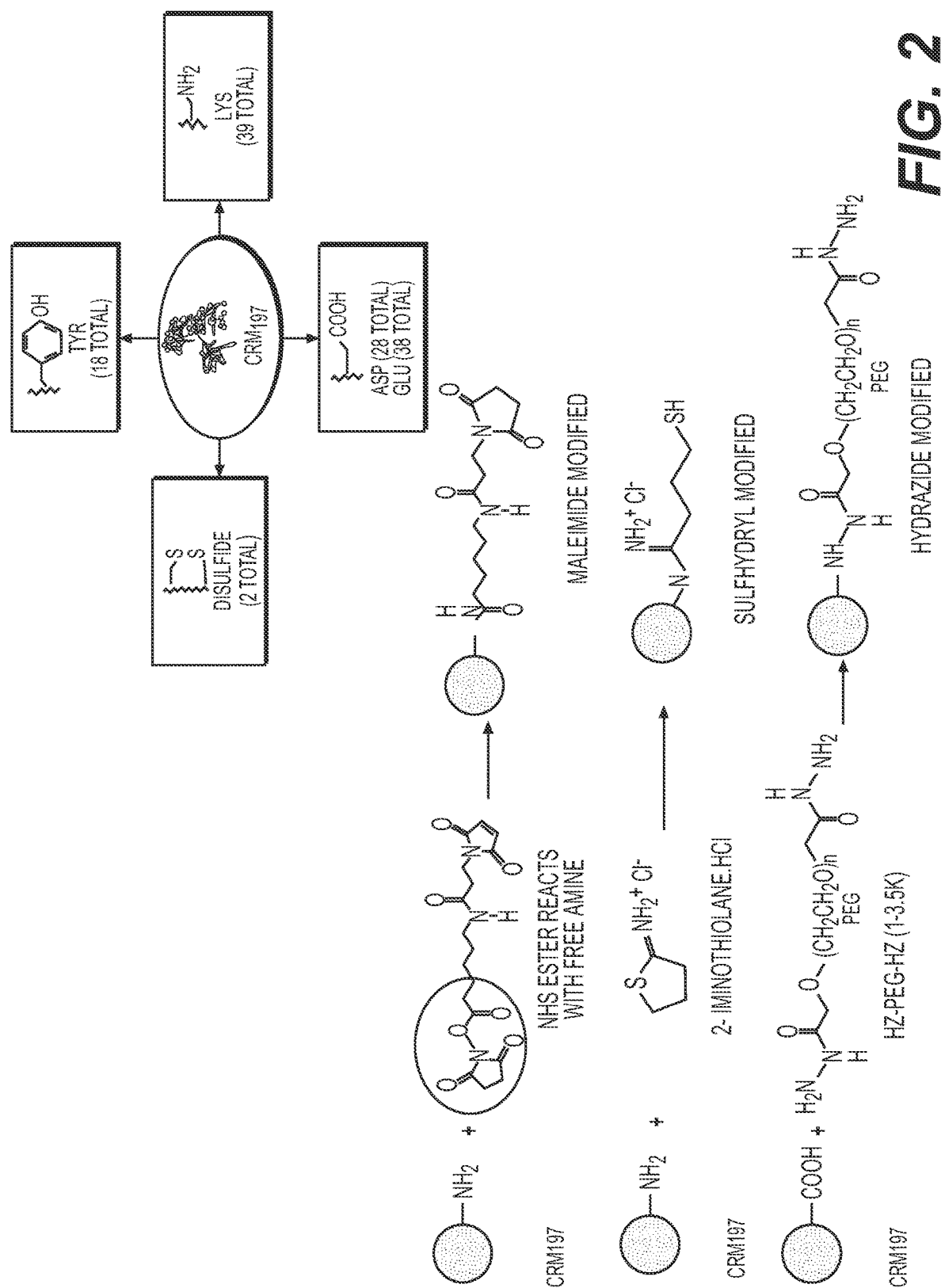

It was surprisingly discovered that a conjugate could be made that provides HPV immunity equivalent to conventional HPV vaccines and with only two doses and with reduced antigens per dose making. The consequence is a vaccine that is five-fold less expensive than conventional vaccines and requires a lower dose making the vaccine more practical and more widely available.

The disclosure is directed to a pharmaceutical conjugate vaccine composition for a human cervical cancer, comprising of virus-like particles preferably derived from L1 HPV clones, conjugated using a spacer arm with a carrier protein, preferably CRM197 and CRM197-like proteins, used in conjugate vaccines and one L2-HPV VLP, and a pharmaceutically acceptable aluminum adjuvant (or non-aluminum adjuvant) and suitable buffer. The conjugate combination comprises combination of L1 and L2 VLPs for the regions where the prevalent infections of those serotypes exist.

The disclosure is directed to immunogenic compositions comprising virus-like particles (VLPs) obtained or derived from L1 and/or L2 proteins of Human papilloma virus (HPV), conjugated with a spacer arm and a carrier protein. Preferably the HPV comprises serotype 6, 11, 16, 18, 31, 33, 45, 52, and/or 58. Preferably the spacer arm comprises a hetero- or homo-bifunctional or multifunctional spacer arm, or in particular, comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$. Preferably the carrier protein comprises tetanus toxoid, diphtheria toxoid, CRM197, tetanus toxoid fragments (TTHc), *N. meningitidis* protein PorB, RSV virus proteins, *B. pertussis* proteins, *pertussis* toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof. Preferably the immunogenic composition comprises an adjuvant, and preferably the adjuvant comprises aluminum salt, calcium phosphate, a liposome of monophosphoryl lipid A (MPLA), saponin QS-21, TLR ligands, and/or a potent TLR4/7/8/9 agonists. Preferred aluminum salts include one or more of aluminum phosphate, aluminum sulfate and/or aluminum hydroxide. Preferably the immunogenic composition, when administered to a patient, boosts the efficacy of a conventional vaccine.

This disclosure comprises an immunogenic composition as described herein wherein the VLP is obtained or derived from HPV L1 protein or HPV L2 protein and the carrier protein is CRM197; wherein the VLPs are bi-valent L1 VLP conjugates, the HPV is serotype 16 and/or 18, and the carrier protein is CRM197; wherein the VLPs are bi-valent L1 VLP conjugates, the HPV is serotype 6 and/or 11, and the carrier protein is CRM197; wherein the VLPs are bi-valent L1 VLP conjugates, the HPV is serotype 31 and/or 33, and the carrier protein is CRM197; wherein the VLPs are bi-valent L1 VLP conjugates, the HPV is serotype 45 and/or 52, and the carrier protein is CRM197; wherein the VLPs are bi-valent L1 VLP conjugates, the HPV is serotype 58, and the carrier protein is CRM197; and wherein the VLPs comprise L1 protein conjugated to L2 protein, and the carrier protein is CRM197.

The present disclosure includes formulation for at least 9-, 10- or higher valent VLP conjugate vaccine which reduces the necessary dose (8-10 µg/dose of individual VLPs compared with 20-40 µg dose used in GARDASIL, Merck or Cerverix, GSK) adsorbed in aluminum phosphate or aluminum hydroxide or other suitable TLR7/8/9 or TLR 4 adjuvants. Examples of VLP-protein conjugates formulations:

VLP1-CRM197-VLP2 (4 and 9-valent L1, 10-valent with L2);

HPV-VLP/CRM197 (monovalent conjugates); and

VLP1-CRM197-VLP2 (4 and 9-valent L1, 10-valent with L2).

Conjugates include conjugation with HBHBSAg as, for example, HBSAg-VLP/CRM197.

The present disclosure is directed to L1 VLP-based 9 valent vaccine candidates as well as addition of L2-VLP based 10 valent vaccines. Four sets of two L1 VLPs are chemically conjugated using a bi-functional spacer arm with a carrier protein (e.g., CRM197 from *E. coli*) and one L1-VLPs conjugated with L2 VLP. L1 and L2-based VLP conjugates can be in general structurally represented as:

L1-XX-VLP-spacer arm-CRM197 L1-XX-VLP

L1-XX-VLP-spacer arm-CRM197 L2-VLP

XX can be any L1 VLP

Examples included are,

L1 VLP16-Spacer arm-CRM197-L1 VLP18

L1 VLP6-spacer arm-CRM197-L1 VLP11

L1 VLP31-spacer arm-CRM197-L1 VLP33

L1 VLP45-spacer arm-CRM197-L1 VLP52

L1 VLP58-spacer arm-CRM197-L2 VLP

The following examples illustrate embodiments of the invention but should not be viewed as limiting the scope of the invention.

EXAMPLES

Example 1

Expression and Purification of Recombinant HPV L1 and L2 VLP in Yeast

L1 protein form all 9 serotypes and L2 protein are expressed in Yeast *Hansenula polymorpha*. Fermentation cycle: ~120 hrs. Expression induced by Methanol using H.P. promoter. The L1 and L2 protein were extracted using yeast cell wall lytic enzymes Zymolase, followed by Benzonase treatment for nucleic acid removal. The extraction step was carried out in TRIS buffer, 20-50 mM, pH 8.5-9.5. The clarified extract (concentration 1 mg/ml, with the L1 protein 150-200 ug/ml), were applied to a cation-exchange chromatography, followed by gel filtration chromatography. In this step, the di-assemble was utilized and assemble step causing the VLP's to assemble in the right configuration and stable molecules. This is confirmed using TEM, The VLPs were stabilized using appropriate buffer. Finally, VLPS are Concentrated using ultrafiltration.

All serotypes L1 VLPs and L2 VLP purification yields are in the region of 7-15% of cell extract, the purified VLPs are 98-99% homogeneous purity. FIG. 2 describes the process flow chart showing the experimental procedures used to purify L1 and L2 HPV serotypes VLPs. All purified VLPs were checked for amino acid sequence, free thiols and lysine's are used with the purpose of stability and site availability for chemical conjugation with carrier proteins.

Example 2

Chemical Conjugation Procedure of L1 and L2 VLPs with CRM197

Chemical conjugation of VLPs are accomplished by the use of chemical cross-linkers, moreover, various conjugation strategies used, for example, use pegylated homo or hetero-bifunctional conjugation reagents having same or two evident reactive groups which can bond to different and distinct functional targets, one on the antigen and the other on the VLP (typically amines or sulfhydryl residues).

Example 3

Activation of CRM197 Using Bi-Functional Spacer Arm

Carrier protein CRM197 activation using pegylated and non-homo or hetero-bifunctional spacer arm. CRM-197 (10 mg/ml) was dissolved in activation buffer, followed by bi-functional spacer arm (see FIG. 1) addition in presence of PB or MES buffer, 80 mM-200 mM, pH 5.8-6.2. Functionalized CRM197 was purified using 10-30 KD TFF cassettes (FIG. 2).

Example 4

Conjugation Process of Functionalized CRM197 to L1 VLP

The basic method steps of conjugation as follows:
1. Chemical conjugation between L1 or L2-VLPs and carrier protein CRM197 (FIG. 3).
2. Evaluation of HPV VLPs integrity after conjugation with CRM197.
3. Analytical characterization of HPV L1 and L2 VLPs and chemically conjugated bi-valent unimolecular or bi-valent VLPS.
4. Formulation of VLP-protein conjugates.
5. Comparison of Immunogenicity with GARDASIL-9.
6. Stability study of VLP conjugates.

Figure 4:
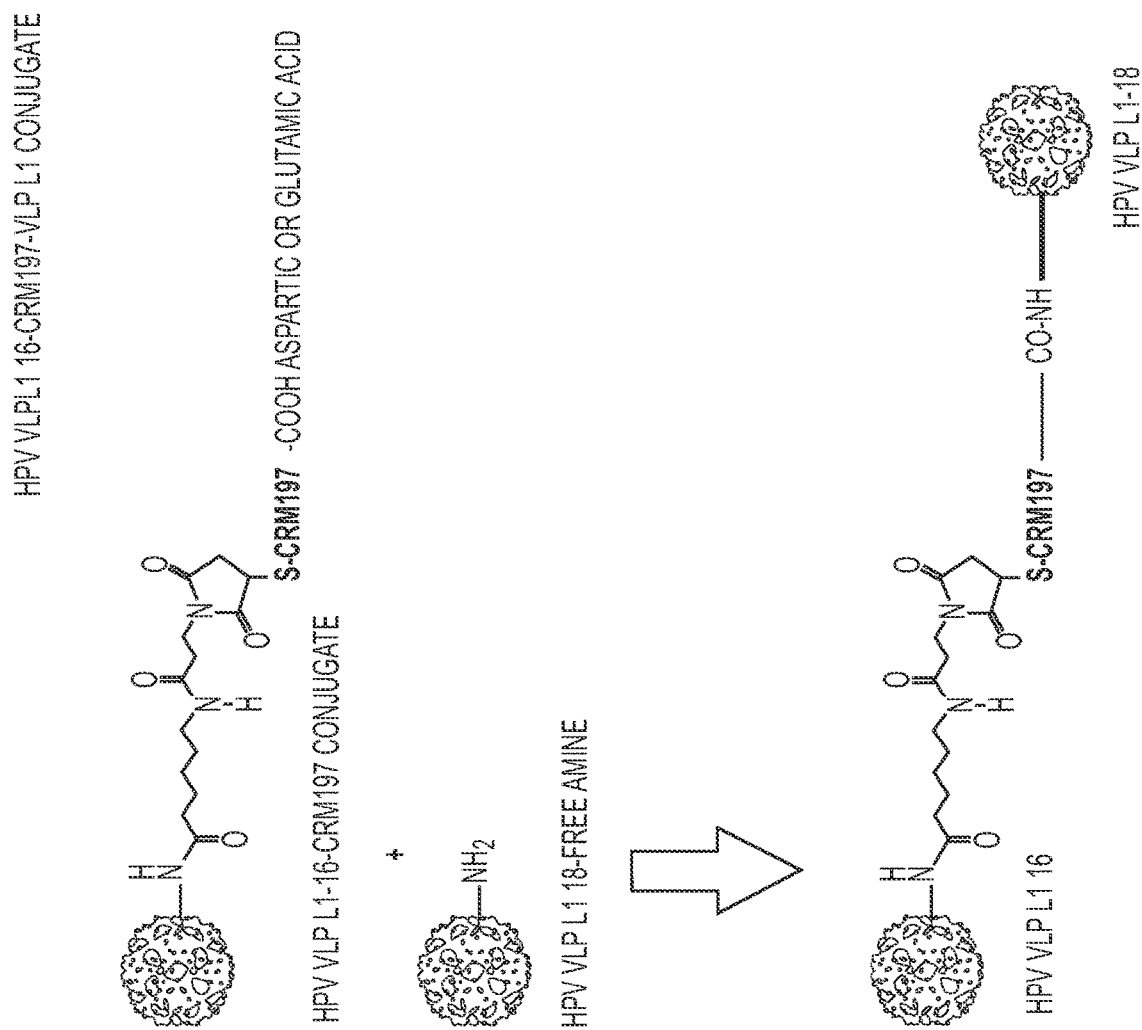
FIG. 4 Schematic of VLP-CRM-VLP conjugate, where HPV VLP L116 type is first conjugates according to scheme 2, followed by VLP L1 18 type is conjugated with VLP L1-CRM197 conjugate.

Examples of conjugates formed include:
I. Conjugation process of L116 HPV-VLP to functionalized CRM197.
II. Conjugation process of L1 HPV 16 VLP-CRM to L1-HPV 18 VLP (FIG. 4),
III. Conjugation process of L1 58 HPV-VLP-CRM197-L2 HPV VLP.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A method for manufacture of an immunogenic composition comprising:
   coupling a first set of L1 or L2 proteins of Human papilloma virus (HPV) to a first set of heterobifunctional, homobifunctional, or multifunctional spacer arms forming a first set of coupled L1 or L2 proteins;
   coupling a second set of L1 or L2 proteins of HPV to a second set of heterobifunctional, homobifunctional, or multifunctional spacer arms forming a second set of coupled L1 or L2 proteins; and
   coupling each of the first and second sets of coupled L1 or L2 proteins to a carrier protein forming the immunogenic composition.

2. The method of claim 1, wherein the L1 or L2 proteins are selected from the group consisting of HPV serotype 6, HPV serotype 11, HPV serotype 16, HPV serotype 18, HPV serotype 31, HPV serotype 33, HPV serotype 45, HPV serotype 52, HPV serotype 58, and combinations thereof.

3. The method of claim 1, wherein the spacer arms comprise $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$, or combinations thereof.

4. The method of claim 1, wherein the carrier protein comprises tetanus toxoid, diphtheria toxoid, CRM197, tetanus toxoid fragments (TTHc), *N. meningitidis* protein PorB, RSV virus proteins, *B. Pertussis* proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof.

5. The method of claim 1, wherein the immunogenic composition comprises an L1 protein and an L2 protein each coupled to the same carrier protein.

6. The method of claim 1, wherein the immunogenic composition comprises two L1 proteins coupled to the same carrier protein.

7. The method of claim 1, wherein the immunogenic composition comprises two L2 proteins coupled to the same carrier protein.

8. The method of claim 1, further comprising formulating the immunogenic composition at about 20-40 µg per dose.

9. The method of claim 1, further comprising formulating the immunogenic composition at about 8-10 µg per dose.

10. A method for manufacture of an immunogenic composition comprising:
    coupling a first set of L1 or L2 proteins of Human papilloma virus (HPV) to a first set of heterobifunctional, homobifunctional, or multifunctional spacer arms forming a first set of coupled L1 or L2 proteins;
    coupling carrier proteins to a second set of heterobifunctional, homobifunctional, or multifunctional spacer arms forming coupled carrier proteins; and
    coupling the first set of coupled L1 or L2 proteins and a second set of L1 or L2 proteins to the coupled carrier proteins forming the immunogenic composition.

11. The method of claim 10, wherein the L1 or L2 proteins are selected from the group consisting of HPV serotype 6, HPV serotype 11, HPV serotype 16, HPV serotype 18, HPV serotype 31, HPV serotype 33, HPV serotype 45, HPV serotype 52, HPV serotype 58, and combinations thereof.

12. The method of claim 10, wherein the spacer arms comprise $NH_2$-PEG-$NH_2$/NHS, NHS/$NH_2$-PEG-COOH, Mal-PEG-$NH_2$, Mal-PEG-NHS, CHO-PEG-CHO, SH-PEG-NH$_2$, ADH, HZ-PEG-HZ, SMPH, SMCC, 4-Arm-PEG-NH$_2$, or combinations thereof.

13. The method of claim 10, wherein the carrier protein comprises tetanus toxoid, diphtheria toxoid, CRM197, tetanus toxoid fragments (TTHc), *N. meningitidis* protein PorB, RSV virus proteins, *B. Pertussis* proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof.

14. The method of claim 10, wherein the immunogenic composition comprises an L1 protein and an L2 protein each coupled to the same carrier protein.

15. The method of claim 10, wherein the immunogenic composition comprises two L1 proteins coupled to the same carrier protein.

16. The method of claim 10, wherein the immunogenic composition comprises two L2 proteins coupled to the same carrier protein.

17. The method of claim 10, further comprising formulating the immunogenic composition at about 20-40 μg per dose.

18. The method of claim 10, further comprising formulating the immunogenic composition at about 8-10 μg per dose.

19. A method for manufacture of an immunogenic composition comprising:
coupling carrier proteins to a first and a second set of heterobifunctional, homobifunctional, or multifunctional spacer arms forming carrier proteins containing multiple spacers arms; and
coupling L1 or L2 proteins of Human papilloma virus (HPV) to the multiple spacer arms of the carrier proteins forming the immunogenic composition.

20. The method of claim 19, wherein the L1 or L2 proteins are selected from the group consisting of HPV serotype 6, HPV serotype 11, HPV serotype 16, HPV serotype 18, HPV serotype 31, HPV serotype 33, HPV serotype 45, HPV serotype 52, HPV serotype 58, and combinations thereof.

21. The method of claim 19, wherein the spacer arms comprises NH$_2$-PEG-NH$_2$/NHS, NHS/NH$_2$-PEG-COOH, Mal-PEG-NH$_2$, Mal-PEG-NHS, CHO-PEG-CHO, SH-PEG-NH$_2$, ADH, HZ-PEG-HZ, SMPH, SMCC, 4-Arm-PEG-NH$_2$, or combinations thereof.

22. The method of claim 19, wherein the carrier proteins comprise tetanus toxoid, diphtheria toxoid, CRM197, tetanus toxoid fragments (TTHc), *N. meningitidis* protein PorB, RSV virus proteins, *B. Pertussis* proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof.

23. The method of claim 19, wherein the immunogenic composition comprises an L1 protein and an L2 protein each coupled to the same carrier protein.

24. The method of claim 19, wherein the immunogenic composition comprises two L1 proteins coupled to the same carrier protein.

25. The method of claim 19, wherein the immunogenic composition comprises two L2 proteins coupled to the same carrier protein.

26. The method of claim 19, further comprising formulating the immunogenic composition at about 20-40 μg per dose.

27. The method of claim 19, further comprising formulating the immunogenic composition at about 8-10 μg per dose.

28. A method for manufacture of an immunogenic composition comprising:
providing L1 or L2 proteins of Human papilloma virus (HPV) and carrier proteins; and
coupling the L1 or L2 proteins and carrier proteins to heterobifunctional, homobifunctional, or multifunctional spacer arms forming the immunogenic composition which comprises the L1 or L2 protein coupled to a spacer arm which is coupled to a carrier protein which is coupled to another spacer arm which is coupled to another L1 or L2 protein.

29. The method of claim 28, wherein the L1 or L2 protein comprises HPV serotypes 6, 11, 16, 18, 31, 33, 45, 52, or 58, and at least one spacer arm comprises a hetero-bifunctional spacer arm, which contains polyethylene glycol and a hydrazide or modified hydrazide.

30. The method of claim 28, wherein the carrier proteins comprises tetanus toxoid or diphtheria toxoid.

* * * * *